T866003

DEFENSIVE PUBLICATION

UNITED STATES PATENT OFFICE

Published at the request of the applicant or owner in accordance with the Notice of Apr. 11, 1968, 849 O.G. 1221. Identification is by serial number of the application and the heading indicates the number of pages of specification, including claims, and of sheets of drawing contained in the application as originally filed. The file of this application is available to the public for inspection; reproduction may be purchased for 30 cents per sheet.

Applications published under the Defensive Publication Program have not been examined as to the merits of alleged invention. The Patent Office makes no assertion as to the novelty of the disclosed subject matter.

PUBLISHED SEPTEMBER 2, 1969

866 O.G. 21

816,168

2,2,4,4-TETRAALKYL-3-THIOXOTHIOBUTYRAMIDES AND DERIVATIVES THEREOF

Edward U. Elam and Herman E. Davis, both of P.O. Box 511, Kingsport, Tenn. 37662

Continuation of application Ser. No. 586,052, Oct. 12, 1966. This application Apr. 9, 1969. Published Sept. 2, 1969

Int. Cl. C07c *153/05*

U.S. Cl. 260—551

No Drawing. 12 Pages Specification

2,2,4,4-tetraalkyl-3-thioxothiobutyramides, having the formula

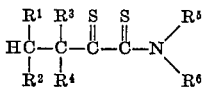

in which $R^1$, $R^2$, $R^3$ and $R^4$, taken singly, is alkyl and in which $R^1$ and $R^2$, when taken collectively with the carbon atom to which they are attached, and $R^3$ and $R^4$ when taken collectively with the carbon to which they are attached, represent alkylene groups completing a saturated carbocyclic ring; $R^5$, when taken singly, is alkyl or aryl, and $R^6$, when taken singly, is hydrogen, alkyl or aryl; $R^5$ and $R^6$, when collectively taken with the nitrogen atom to which they are attached, represent a saturated heterocyclic ring, which are useful as epoxy polymerization catalysts, are prepared by reacting a 4-alkylidene-3,3-dialkyl-2-thietanethione with an amine. The use of primary amines in the above reaction also produces 2,2,4,4-tetraalkyl-3-iminothiobutyramides of the formula

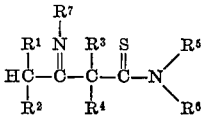

and iminothiobutyramides of the formula

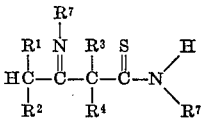

wherein $R^7$ is alkyl or aryl. The 2,2,4,4-tetraalkyl-3-thioxothiobutyramides may form dimers of the formula

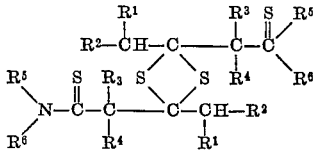

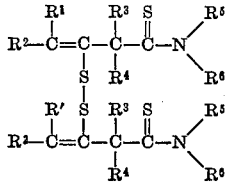

or be oxidized by air to 3,3′(dithio)bis[2,2,4,4-tetraalkyl-3-buteneamides] of the formula